US012295622B2

(12) United States Patent
Faulhaber

(10) Patent No.: US 12,295,622 B2
(45) Date of Patent: *May 13, 2025

(54) SPINAL ANCHORING SYSTEM

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 315 days.

This patent is subject to a terminal disclaimer.

(21) Appl. No.: 17/729,234

(22) Filed: Apr. 26, 2022

(65) Prior Publication Data
US 2022/0249132 A1 Aug. 11, 2022

Related U.S. Application Data

(63) Continuation of application No. 16/696,064, filed on Nov. 26, 2019, now Pat. No. 11,350,971, which is a
(Continued)

(51) Int. Cl.
A61B 17/70 (2006.01)
A61B 17/16 (2006.01)
A61B 17/56 (2006.01)
A61B 17/86 (2006.01)
A61B 17/88 (2006.01)

(52) U.S. Cl.
CPC ........ A61B 17/705 (2013.01); A61B 17/1671 (2013.01); A61B 17/7032 (2013.01); A61B 17/7034 (2013.01); A61B 17/7037 (2013.01); A61B 17/7044 (2013.01); A61B 17/7082 (2013.01); A61B 17/8605 (2013.01); A61B 17/56 (2013.01); A61B 2017/564 (2013.01); A61B 17/7001 (2013.01);
(Continued)

(58) Field of Classification Search
CPC .................. A61B 17/7049; A61B 17/7058
See application file for complete search history.

(56) References Cited

U.S. PATENT DOCUMENTS 6,866,664 B2 * 3/2005 Schar et al. ....... A61B 17/7052
606/252
8,211,151 B2 7/2012 Schwab et al.
(Continued)

FOREIGN PATENT DOCUMENTS

JP 2002-102241 A 4/2002
JP 2007-531588 A 11/2007
(Continued)

Primary Examiner — Ellen C Hammond

(57) ABSTRACT

An anchoring system for implanting in bone, the system comprising a first coupling assembly having a first clamp and a first coupling body that receives and holds a first stabilization element; a second coupling assembly that receives and holds a second stabilization element; and a plate that attaches to the first coupling assembly and the second coupling assembly, wherein the first coupling assembly attaches to a bone fastener, and wherein the first coupling body includes a cap retainer that receives a locking cap that applies a directional force to force the first coupling body toward the plate, and applies another directional force to force the first clamp toward the plate, thereby fixedly securing the first coupling body and the first clamp to the plate.

20 Claims, 12 Drawing Sheets

Related U.S. Application Data continuation of application No. 15/823,655, filed on Nov. 28, 2017, now Pat. No. 10,517,648, which is a continuation of application No. 14/874,550, filed on Oct. 5, 2015, now Pat. No. 9,855,078.

(52) U.S. Cl.
CPC ... *A61B 17/7058* (2013.01); *A61B 2017/8655* (2013.01); *A61B 17/88* (2013.01)

(56) References Cited

U.S. PATENT DOCUMENTS

| | | | | |
|---|---|---|---|---|
| 8,556,942 B2* | 10/2013 | Ziolo | ............... | A61B 17/7058 606/280 |
| 9,603,635 B2* | 3/2017 | Leff | ............... | A61B 17/7056 |
| 11,684,395 B2* | 6/2023 | Loftis | ............... | A61B 17/7011 606/264 |
| 11,707,304 B2* | 7/2023 | Lee | ............... | A61B 17/7034 606/250 |
| 11,793,554 B2* | 10/2023 | Carruth | ............... | A61B 17/7001 |
| 2002/0049446 A1 | 4/2002 | Harkey et al. | | |
| 2004/0006342 A1* | 1/2004 | Altarac | ............... | A61B 17/7041 606/264 |
| 2005/0228326 A1 | 10/2005 | Kalfas et al. | | |
| 2006/0064091 A1* | 3/2006 | Ludwig | ............... | A61B 17/701 606/279 |
| 2009/0259254 A1* | 10/2009 | Pisharodi | ............... | A61B 17/7037 606/264 |
| 2009/0281576 A1* | 11/2009 | Weaver | ............... | A61B 17/7007 606/301 |
| 2010/0222779 A1* | 9/2010 | Ziemek | ............... | A61B 17/7055 606/71 |
| 2011/0190824 A1* | 8/2011 | Gephart | ............... | A61B 17/7002 606/246 |
| 2011/0245883 A1 | 10/2011 | Dall et al. | | |
| 2012/0071926 A1* | 3/2012 | Jani | ............... | A61B 17/7049 606/279 |
| 2012/0226316 A1* | 9/2012 | Dant | ............... | A61B 17/7052 606/264 |
| 2015/0282846 A1* | 10/2015 | Richelsoph | ............... | A61B 17/7035 606/287 |
| 2017/0112540 A1* | 4/2017 | Montello | ............... | A61B 17/7032 |
| 2018/0014863 A1* | 1/2018 | Biester | ............... | A61B 17/7001 |
| 2018/0325558 A1* | 11/2018 | Yacoub | ............... | A61B 17/8816 |

FOREIGN PATENT DOCUMENTS

| | | |
|---|---|---|
| JP | 2012-507316 A | 3/2012 |
| WO | 2010052462 A1 | 5/2010 |

\* cited by examiner

SPINAL ANCHORING SYSTEM

CROSS REFERENCE TO RELATED APPLICATION

This application is a continuation of U.S. Ser. No. 16/696,064, filed on Nov. 26, 2019 (published as U.S. Pat. Pub. No. 2020-0093516), which is a continuation of U.S. Ser. No. 15/823,655, filed on Nov. 28, 2017, now issued as U.S. Pat. No. 10,517,648, which is a continuation of U.S. Ser. No. 14/874,550, filed on Oct. 15, 2015, now issued as U.S. Pat. No. 9,855,078, which are incorporated herein by reference in their entireties.

FIELD OF THE DISCLOSURE

The present disclosure relates to bone fixation devices that may include a stabilization element and a bone fastener with a variable angle coupling assembly; and, more particularly, to an anchoring system that aids in, for example, posterior segmental fusion by improving stabilization and rigidity in implant constructs that include, e.g., poly-axial bone screws.

BACKGROUND OF THE DISCLOSURE

Often, severe pain or damage to the nervous system is caused by spinal abnormalities. Also, movement of the spinal column may be significantly limited by such abnormalities. Many of these abnormalities may be the result of, for example, trauma or degenerative disc disease. Known treatments of such abnormalities typically involve affixing screws or hooks to one or more vertebrae and connecting the screws or hooks to a rod that is aligned with the longitudinal axis of the spinal column to immobilize the spinal segments with respect to each other. Pedicle screw systems are frequently used to provide spinal fixation.

A number of pedicle screw systems are known, which share common techniques and principles of screw placement and rod attachment. Generally, bone screws are screwed into pedicles of vertebrae and coupled to at least one elongated rod. The pedicles, which consist of a strong shell of cortical bone and a core of cancellous bone, are generally used for the bone screw sites because they provide the strongest point of attachment of a spine and, thereby, the greatest resistance against bone-metal junction failure. The bone screws may be positioned so as to traverse all three columns of the vertebrae, thereby providing ventral and dorsal stability in the spine.

Known pedicle screw systems typically include pedicle screws and rods to stabilize adjacent spinal segments. Such systems also include variable angled coupling caps (or heads) on the pedicle screws to allow for angular adjustment of the coupling mechanism between the rod and screws. Since pedicle size and angulation varies throughout the spinal column, several different sizes and shapes of pedicle screws are used in these systems. These systems are generally designed to provide stable and rigid structures to promote bone growth and fusion.

Recovery from spinal surgery is typically a long and arduous process that places severe restrictions on patient mobility. The recovery process may be significantly affected by stress factors directed to, for example, pedicle screw systems and rods by the patient's body. The stress factors may affect, for example, spinal fusion rates, recovery time, patient mobility, and the like. Accordingly, a need exists for systems and methodologies that improve patient recovery and reduce recovery time after surgery.

SUMMARY OF THE DISCLOSURE

The present disclosure is generally directed towards an improved anchoring system that, among other things, aids in posterior segmental fusion by adding increased stability and rigidity to promote fusion in implant constructs. The anchoring system allows a plurality of rods (e.g., two rods) to be mounted to one poly-axial screw. Exemplary embodiments of the anchoring system may include a bone screw system that may attach to and support two or more rods to provide superior stabilization and rigidity in implant constructs.

According to a non-limiting aspect of the disclosure, an anchoring system for implanting in bone is disclosed. The anchoring system comprises a first coupling assembly that receives and holds a first stabilization element; a second coupling assembly that receives and holds a second stabilization element; and a plate that attaches to the first coupling assembly and the second coupling assembly, wherein the first coupling assembly attaches to a bone screw. The first coupling assembly, the second coupling assembly, and the plate may be substantially simultaneously rotationally and/or angularly adjustable with respect to the bone screw.

The first coupling assembly may comprise: a first coupling body that may receive and hold the first stabilization element; and a first clamp that may fasten the first coupling body to the plate. At least one of the first coupling body and the first clamp may include a float area to allow the first coupling body to rotate with respect to the first clamp. The first coupling assembly may include a saddle that attaches to the first clamp.

The second coupling assembly may comprise: a second coupling body that may receive and hold the second stabilization element; and a second clamp that may fasten the second coupling body to the plate.

The first coupling body and the second coupling body may be independently rotatable when the first coupling assembly is attached to a bone screw.

The plate may comprise: a plate-coupling lock that locks the plate to the first coupling body; and a plate-clamp lock that locks the plate to the first clamp.

The first coupling body may comprise a coupling-plate lock that may contact and engage the plate-coupling lock to lock the plate to the first coupling body.

The first clamp may comprise a clamp-plate lock that may contact and engage the plate-clamp lock to lock the plate to the first clamp.

The plate-coupling lock may include male locking features and the plate-clamp lock may include female locking features.

The first coupling body may include a cap retainer that receives a locking cap that may transfer and apply a force in a first direction to a portion of the first stabilization element and to a portion of the saddle, wherein the first direction is towards the first clamp. The force may cause the first clamp to travel in a second direction to lock the first clamp to the plate, wherein the second direction is substantially opposite to the first direction.

According to another non-limiting aspect of the disclosure, an anchoring system for implanting in bone is provided that comprises: a first coupling assembly having a first clamp and a first coupling body that receives and holds a first stabilization element; a second coupling assembly that receives and holds a second stabilization element; and a plate that attaches to the first coupling assembly and the second coupling assembly, wherein the first coupling assembly attaches to a bone fastener, and wherein the first coupling body includes a cap retainer that receives a locking cap that applies a directional force to force the first coupling body toward the plate, and applies another directional force to force the first clamp toward the plate, thereby fixedly securing the first coupling body and the first clamp to the plate. The second coupling assembly may comprise: a second coupling body that receives and holds the second stabilization element; and a second clamp that fastens the second coupling body to the plate. The first coupling body and the second coupling body may be independently rotatable when the first coupling assembly is attached to a bone fastener. At least one of the first coupling body and the first clamp may include a float area to allow the first coupling body to rotate with respect to the first clamp. The first coupling assembly may further comprise a saddle that attaches to the first clamp. The plate may comprise: a plate-coupling lock that locks the plate to the first coupling body; and a plate-clamp lock that locks the plate to the first clamp.

According to a further non-limiting aspect of the disclosure, an anchoring system is provided that comprises: a first coupling assembly having a first clamp and a first coupling body that receives and holds a first stabilization element; a second coupling assembly that receives and holds a second stabilization element; and a plate having a plate-coupling lock and a plate-clamp lock to fixedly secure the first coupling assembly and the second coupling assembly to the plate. The anchoring system may comprise a bone fastener that couples to either the first coupling assembly or the second coupling assembly.

Additional features, advantages, and embodiments of the disclosure may be set forth or apparent from consideration of the detailed description and drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to help explain the principles of the disclosure. No attempt is made to show structural details of the disclosure in more detail than may be necessary for a fundamental understanding of the disclosure and the various ways in which it may be practiced. In the drawings.

Figure 1A:
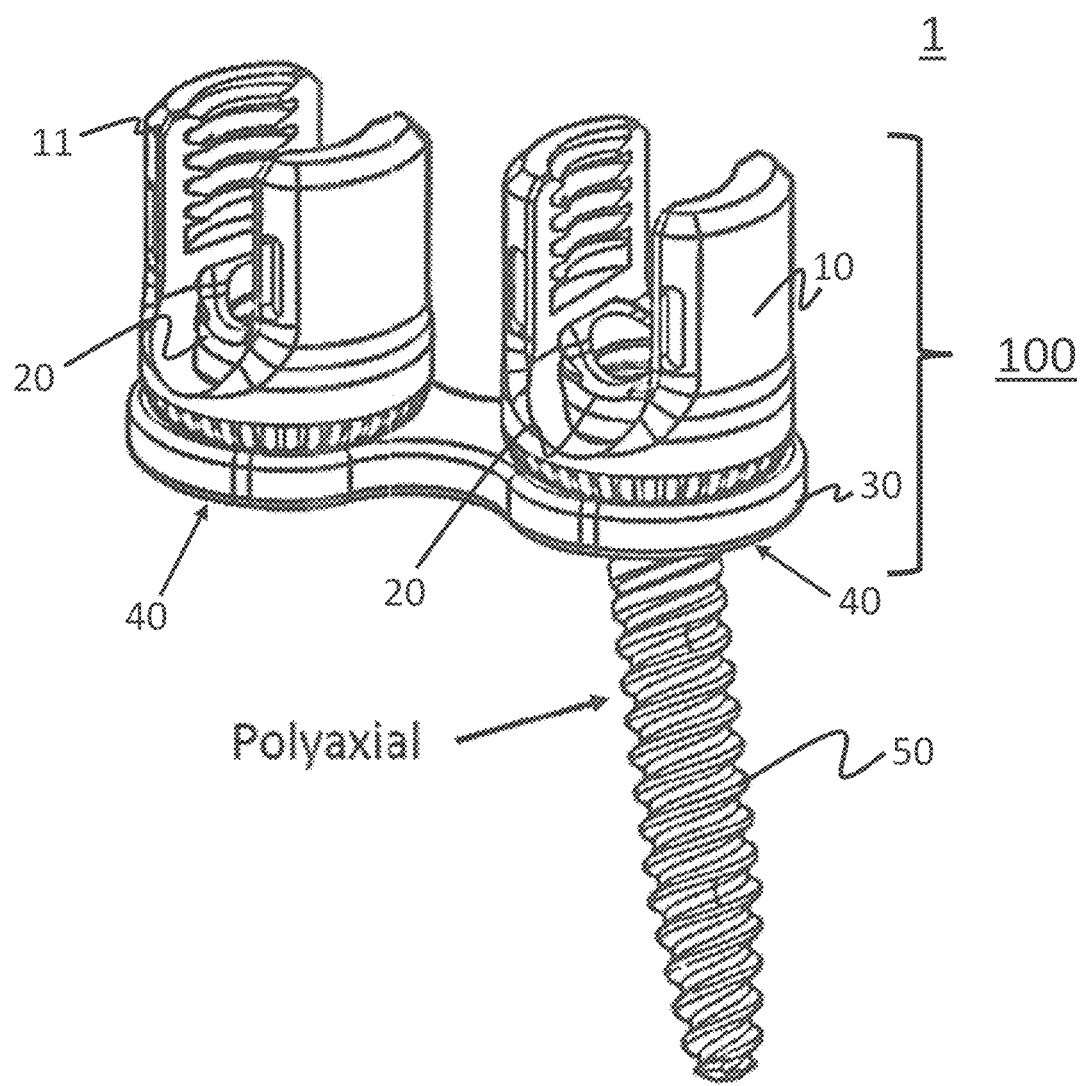
FIGS. 1A and 1B show different views of an exemplary embodiment of an anchoring system.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

Figure 1B:
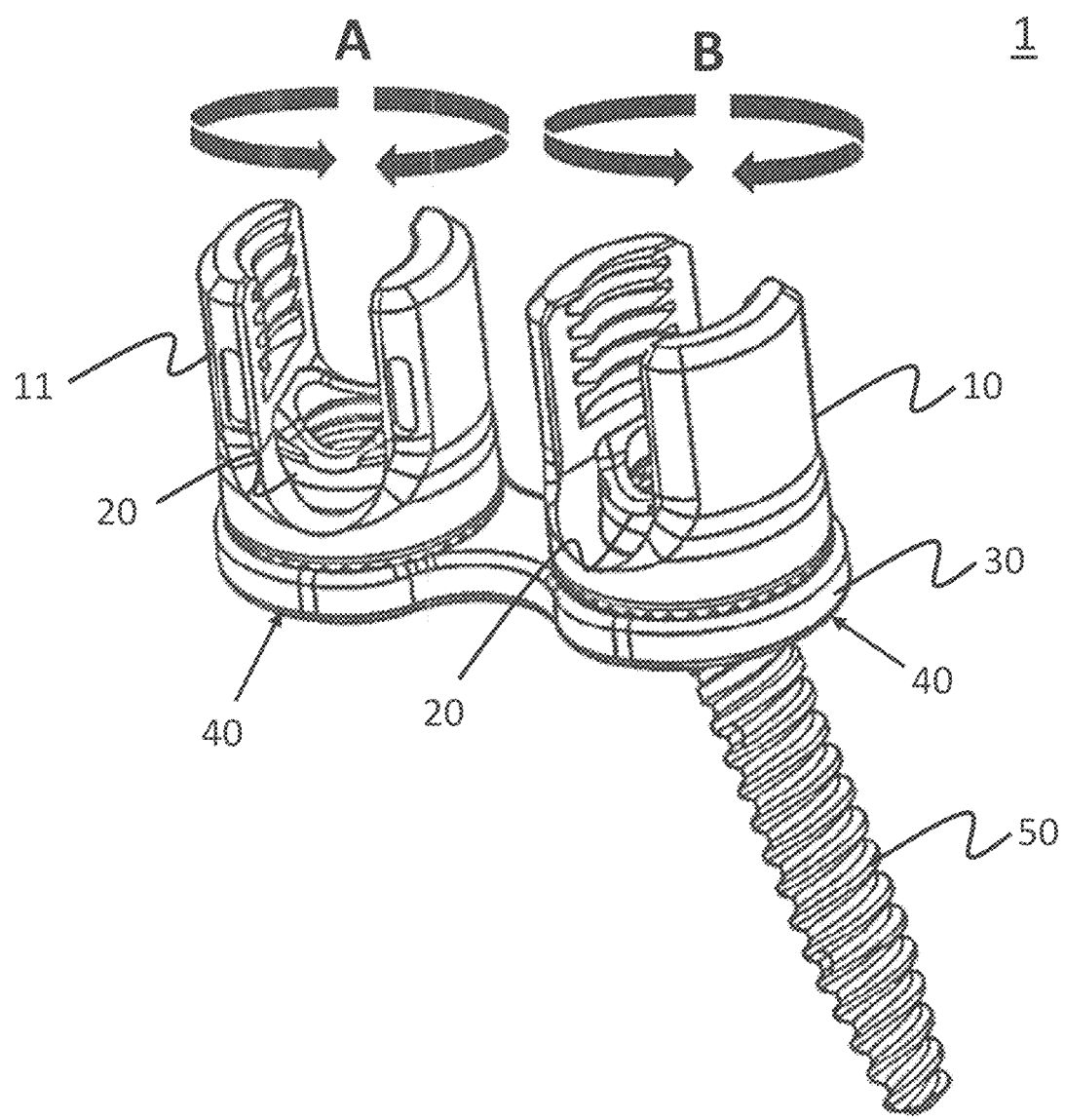
Figure 6A:
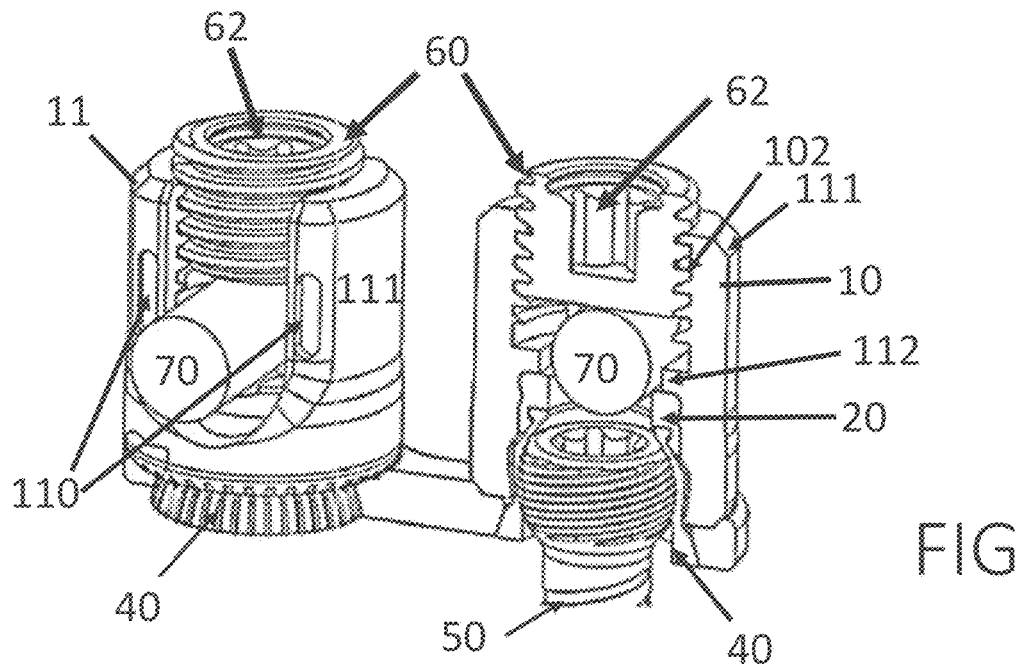
FIGS. 6A and 6B show cross-section views of the anchoring system in FIGS. 1A and 1B, provided with a pair of locking caps and a pair of stabilization elements.
Figure 6B:
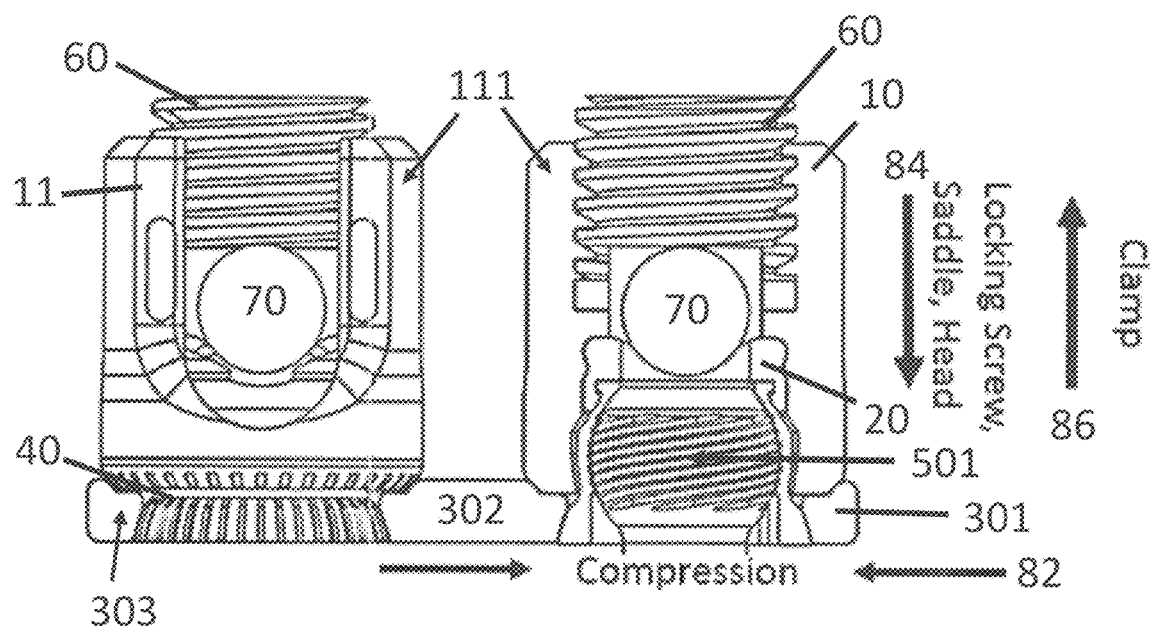

FIGS. 1A and 1B show different views of an embodiment of an anchoring system 1; and, FIGS. 6A and 6B show cross-section views of the anchoring system 1 provided with a pair of locking caps 60 and a pair of stabilization elements 70.

As illustrated in FIGS. 1A-1B and 6A-6B, the anchoring system 1 comprises a plate assembly 100 and a bone fastener 50. The plate assembly 100 comprises a pair of coupling assemblies 10 and 11, and a plate 30. It is noted that the plate assembly 100 may comprise additional coupling assemblies (not shown). The coupling assemblies 10 and 11 may be substantially the same, or they may differ from each other without departing from the scope or spirit of the disclosure. The coupling assemblies 10 and 11 may couple stabilization element(s) 70 to the bone fastener 50.

The stabilization element(s) 70 may include, for example, an elongate rod, a pin (not shown), a brace (not shown), a spring (not shown), a cord (not shown), a resilient extension (not shown), or any other stabilization device that may be coupled to the plate assembly 100 to provide stabilization. One or more locking caps 60 may be used to secure the stabilization elements 70 in the coupling assemblies 10 and 11, as illustrated in FIGS. 6A and 6B. The various components of the anchoring system 1 may be made of a material such as, for example, stainless steel, titanium, titanium-alloy, or the like.

The coupling assemblies 10 and 11 are configured to be independently rotatable with respect to each other and the plate 30, as noted by rotation arrows A and B in FIG. 1B. The plate assembly 100, including the coupling assemblies 10, 11, is configured to be adjustable with respect to the longitudinal axis of the bone fastener 50. For instance, the plate assembly 100 is configured to be rotationally and angularly adjustable with respect to the bone fastener 50, including the longitudinal axis thereof, when non-lockably coupled to the bone fastener 50. The coupling assembly 10 (or 11) in the plate assembly 100 is configured to conformingly and movably receive a head portion 501 of the bone fastener 50, as illustrated in FIG. 2.

Figure 2:
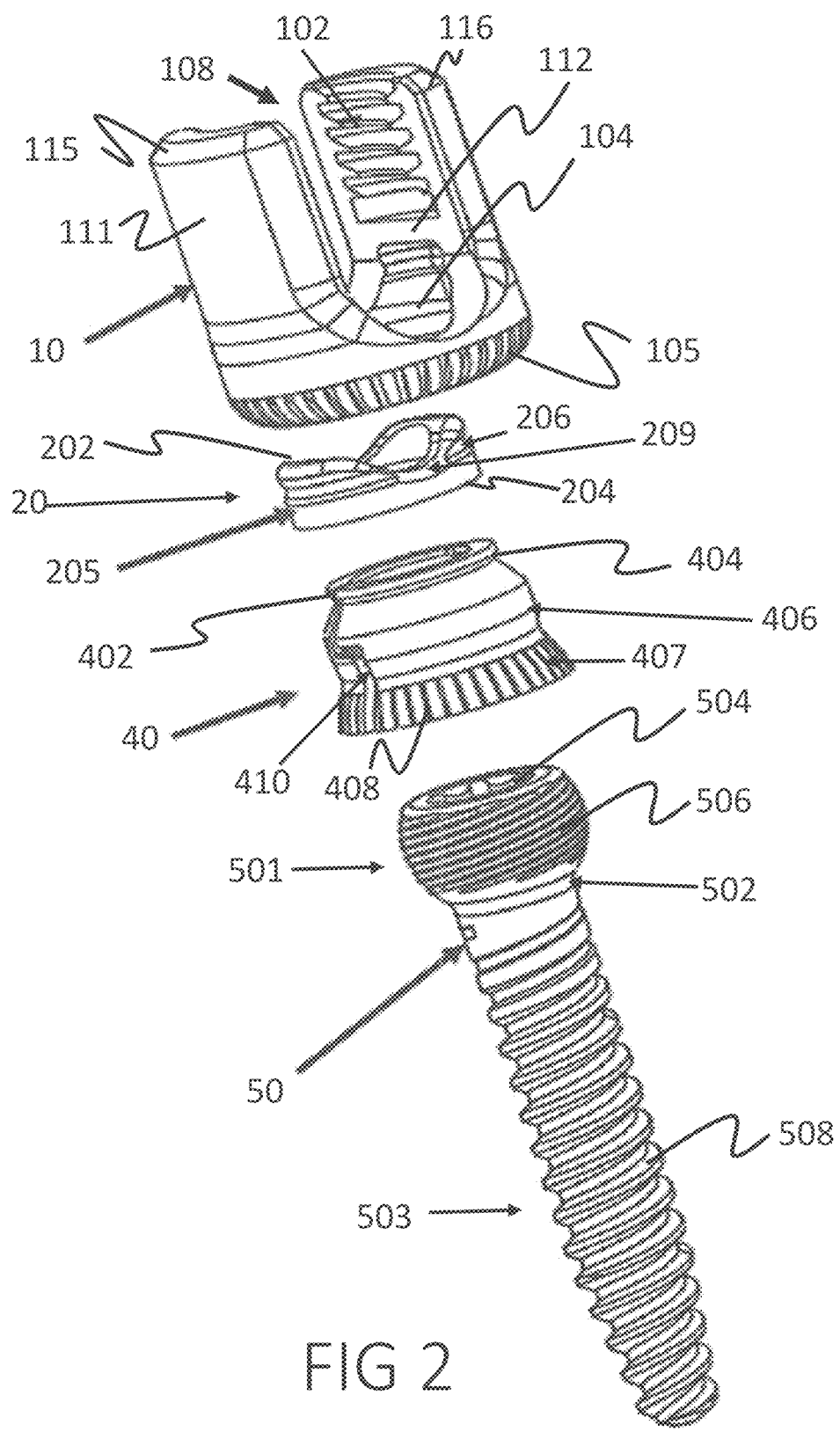
FIG. 2 shows an exploded view of a portion of the exemplary embodiment of the anchoring system in FIGS. 1A and 1B.

FIG. 2 shows an exploded view of a portion of the anchoring system 1 without the plate 30. The coupling assembly 10 (or 11) includes a coupling body 111, a saddle 20, and a clamp 40. As seen, the coupling body 111 may have a "tulip" shape.

At its proximal end, the coupling body 111 includes a pair of upwardly extending arms 115, 116 and a slot 108 between the extending arms 115, 116. At its distal end, the coupling body 111 includes a receptacle 104 formed in the coupling body 111, and a coupling-plate lock 105 provided on, for example, the distal end surface of the coupling body 111. The slot 108 may be configured to receive the stabilization element 70, as illustrated in FIGS. 6A and 6B. The coupling body 111 is configured to receive and hold the locking cap 60 at the proximal end, as seen in FIGS. 6A and 6B. The coupling body 111 may hold the locking cap 60 in a predetermined location in the longitudinal direction after insertion in the coupling body 111, so that a contact surface of the locking cap 60 contacts and presses upon a surface of the stabilization element 70 to hold the stabilization element 70 in a fixed position, preventing the element 70 from moving rotationally, angularly or longitudinally along a longitudinal axis of the stabilization element 70, when the anchoring system 1 is installed and secured. The coupling body 111 includes a cap retainer 102 at its proximal end, which in the embodiment illustrated in, for example, FIG. 2, includes a threading provided on the interior surfaces of the upwardly extending arms 115, 116. Alternatively, the cap retainer 102 may include, for example, a tongue and grove mechanism, or any other retaining mechanism that can secure a locking cap 60 and hold it fixedly in a predetermined location in the coupling body 111.

Figure 3A:
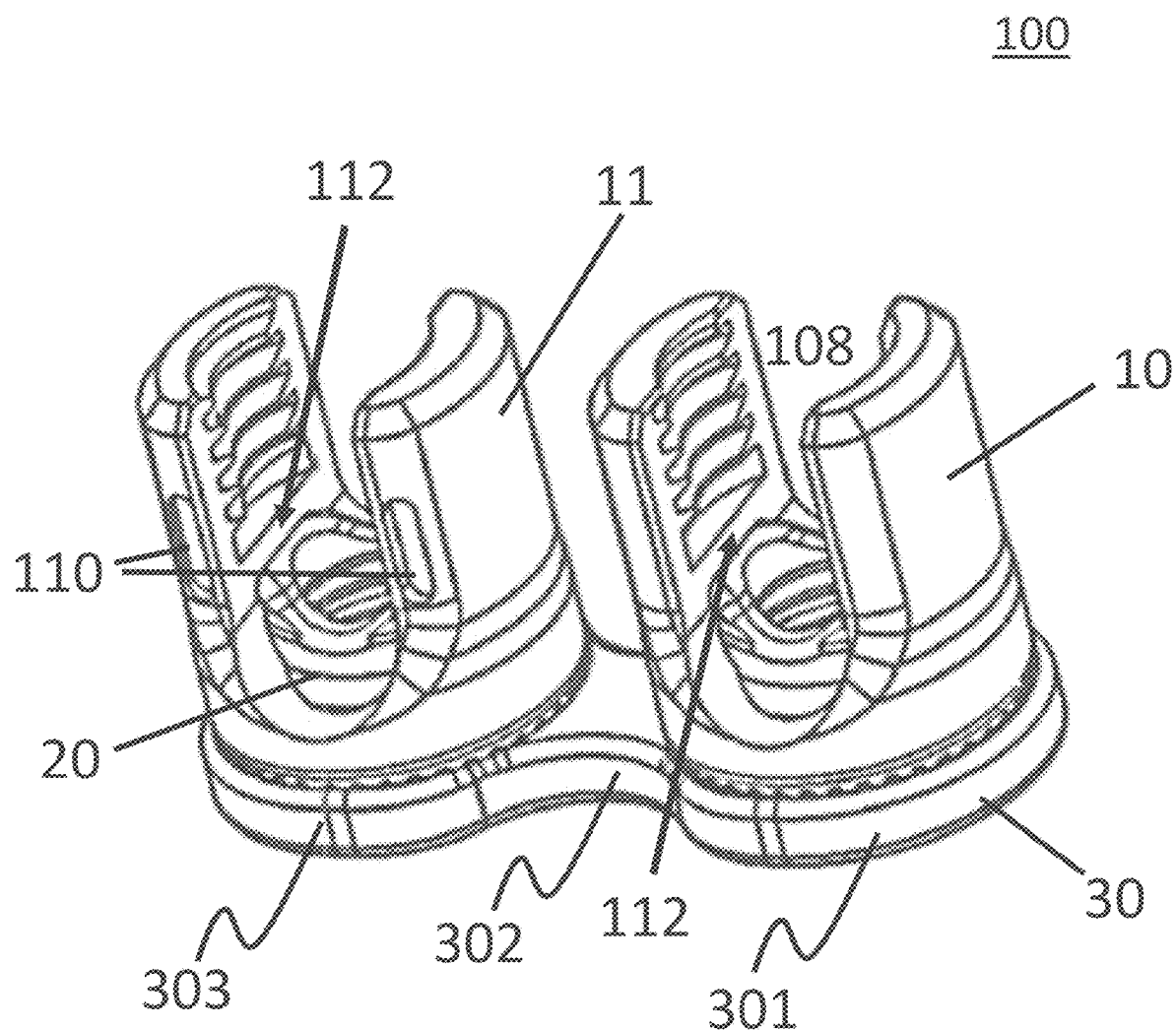
FIGS. 3A and 3B show perspective and exploded views, respectively, of an exemplary embodiment of a plate assembly that may be included in the anchoring system in FIGS. 1A and 1B.
Figure 3B:
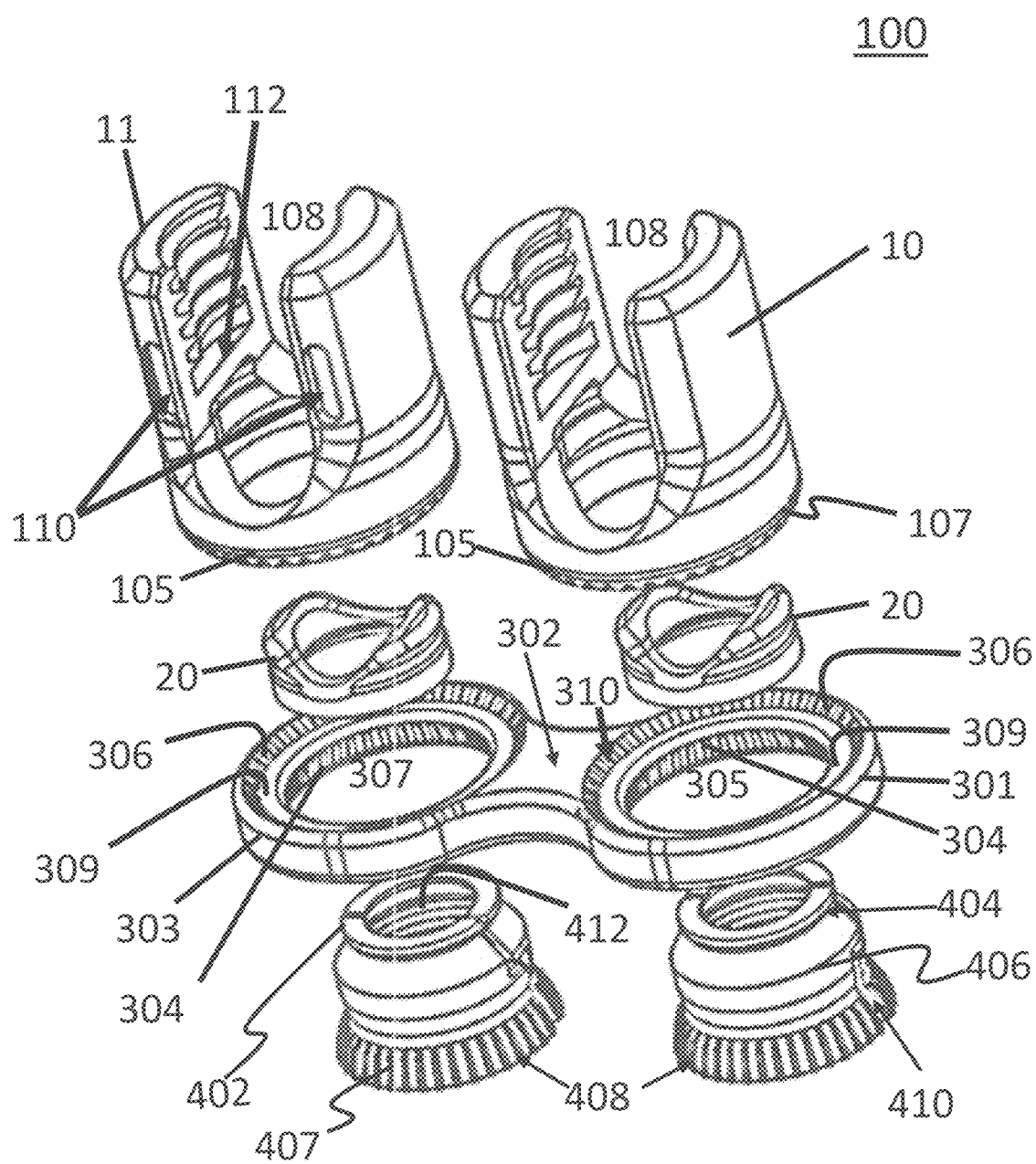

FIGS. 3A and 3B show an assembled view and an exploded view, respectively, of the plate assembly 100, including the coupling assemblies 10, 11, and plate 30.

Referring to FIGS. 2, 3A and 3B, the upwardly extending arms 115, 116 of the coupling body 111 may extend longitudinally in a superior direction and include an interior, an exterior, and upper surfaces. One or both of the extending arms 115, 116 may include one or more tool-receiving recesses 110, as illustrated in FIG. 3A, to receive and engage corresponding protrusions on a driver tool (not shown) and be driven by the tool to rotate and/or angularly adjust the coupling body 111. Alternatively, or additionally, one or both extending arms 115, 116 may include tool-engaging protrusions (not shown) that may contact and engage corresponding recesses on the driver tool (not shown) to be driven by the tool to rotate and/or angularly adjust the coupling body 111.

The coupling-plate lock 105 may be provided on the distal end portion of the coupling body 111 and configured to contact and engage a corresponding plate-coupling lock 306 provided on the plate 30, as seen in FIG. 3B. For instance, the coupling-plate lock 105 may include female (or male) locking features 107 that are configured to contact and engage the plate-coupling lock 306, which may include corresponding male (or female) locking features 310, thereby securing and locking the coupling body 111 with respect to the plate 30.

According to a non-limiting embodiment of the disclosure, the male locking features 310 (or 107) may include, for example, teeth and the female locking features 107 (or 310) may include, for example, corresponding receivers that are configured to receive and engage the teeth. The teeth may have any shape that is suitable to engage corresponding receivers for the teeth, including, for example, a semispherical shape, a rectangular shape, a pyramid shape, a cylinder shape, a diamond shape, an elliptical shape, or the like. The corresponding receivers for the teeth may include corresponding recesses that are configured to receive and securely hold the teeth, including, for example, a semispherical shaped recess, a rectangular shaped recess, a pyramid shaped recess, a cylindrical shaped recess, a diamond shaped recess, an elliptical shaped recess, or the like.

Referring back to FIG. 2, the coupling body 111 may include a stop 112, or other limiting mechanism, to prevent the locking cap 60 (shown in FIGS. 6A and 6B) from moving past a certain point and/or from moving back (e.g., rotating back) from a predetermined engaged position whereby the locking cap 60 exerts a force on the stabilization element 70. The stop 112 may be integrally formed in the interior surface of one or both of the extending arms 115, 116. As seen in FIGS. 6A and 6B, as the locking cap 60 is inserted (e.g., rotated from a first position to a second position), the stop 112 would prevent the cap 60 from moving past the stop 112.

The stop(s) 112 may form a wall portion of the receptacle 104, which may function as a stop for the saddle 20. The width (or space) between the stops 112 in the coupling body may be substantially the same as the width of the slot 108. The width between the stops 112 (and/or the width of the slot 108) in the coupling body 111 may be determined based on, for example, a diameter of the stabilization element 70 to be used with the anchoring system 1, so as to facilitate guiding and centering the stabilization element 70 during installation, which may be guided to and seated on a proximal surface portion 202 (shown in FIG. 2) of the saddle 20, as illustrated in FIGS. 6A and 6B.

The saddle 20 is configured to be inserted into and retained in the receptacle 104 of the coupling body 111. The saddle 20 may include an annular body. The saddle 20 may be made of an elastic or compressible material that is suitable for in vivo applications, as understood by those skilled in the art. The saddle 20 may facilitate in securing the coupling assembly 10 (or 11) to the clamp 40 and/or the bone fastener 50, as well as providing a seat for the stabilization element 70. The saddle 20 includes the proximal surface portion 202, which may include a stabilization element receiving channel 209, a distal surface portion 204, and the perimeter wall 205, where the distal surface portion 204 is opposite to the proximal surface portion 202. The stabilization element receiving channel 209 may be shaped to match the shape of the stabilization element 70, thereby providing a substantially snug, contoured fit for the stabilization element 70 against the surface portion 202 when the plate assembly 100 is installed and secured, as discussed below. A part of the proximal surface portion 202 may be shaped to match the shape of the stop(s) 112, thereby providing a substantially snug, contoured fit with the stop(s) 112. The matching shape of the surface portion 202 helps to provide a more compact coupling body 111, and to provide for improved rigidity of the stabilization element 70 when the element is secured in the coupling body 111 by the locking cap 60. The outer surface of the perimeter wall 205 of the saddle 20 may be configured to match the contour of an inner wall surface of the receptacle 104. The distal surface portion 204 may include a lip portion 214 (shown in FIGS. 5A and 5B), which may be formed in an inner wall of the perimeter wall 205. The lip portion 214 may be configured to engage and fasten to a corresponding lip portion 404 (shown in FIGS. 5A and 5B) of the clamp 40.

Figure 5A:
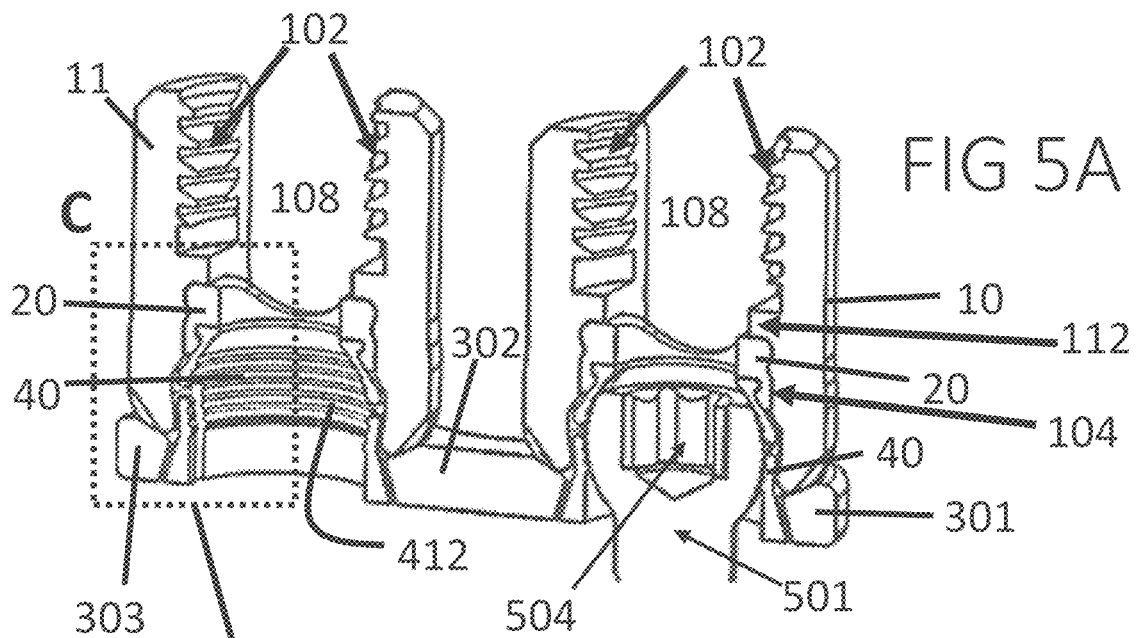
FIGS. 5A and 5B show cross-section views of a portion of the exemplary embodiment of the anchoring system in FIGS. 1A and 1B.
Figure 5B:
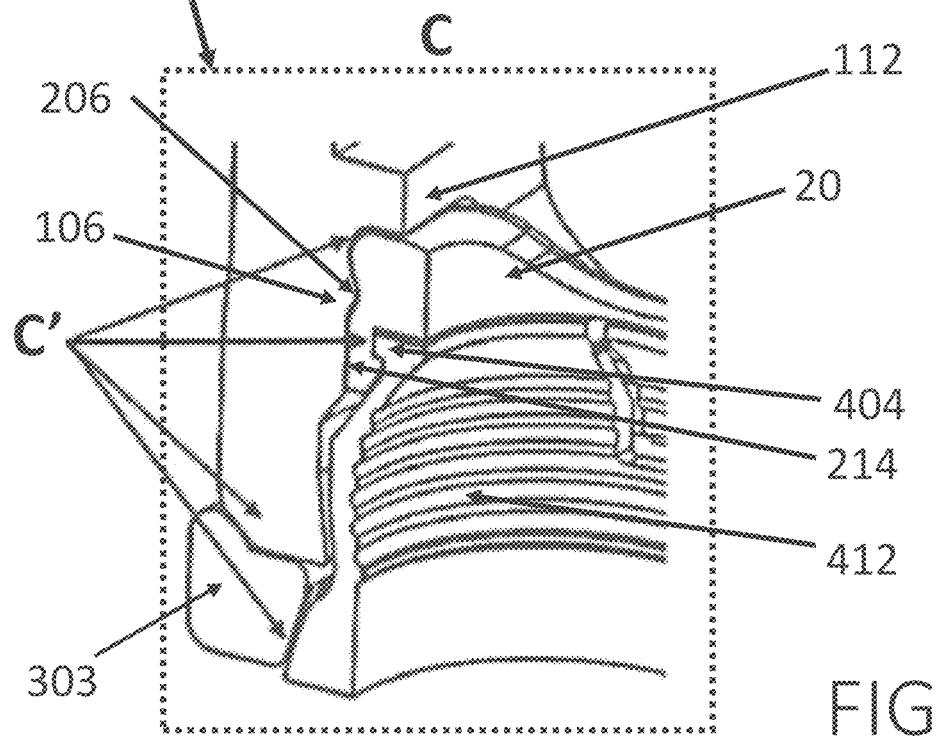

FIGS. 5A and 5B show cross-section views of a portion of the anchoring system 1, including the plate assembly 100, which comprises the coupling assemblies 10 and 11. FIG. 5B shows a detailed view of section C in FIG. 5A.

Referring to FIGS. 2, 5A, and 5B, the receptacle 104 may be configured to receive and hold the saddle 20 and at least a portion of the clamp 40. The receptacle 104 may be formed in the lateral direction by an inner wall of the coupling body 111, and the stop 112 in the superior direction of the coupling body 111, which is substantially normal to the lateral direction. The walls of the receptacle 104 may be contoured to match the contours of the saddle 20 and/or clamp 40, so as to provide a snug and secure fit for the saddle 20 and/or clamp 40 in the receptacle 104 when the plate assembly is installed and secured.

The receptacle 104 may include a protrusion 106 (e.g., tongue) that may be configured to engage a corresponding recess 206 (e.g., grove) provided in the saddle 20, so as to engage and hold the saddle 20 in a predetermined orientation and/or location in the coupling body 111. The protrusion 106 may be configured to facilitate aligning of the saddle 20, so that the stabilization receiving channel 209 (shown in FIG. 2) is aligned with, for example, the slot 108, and aligned to match and contact a surface of the stabilization element 70 when it is installed in the slot 108 of the coupling body 111.

Alternatively, the receptacle 104 may include a recess (e.g., grove) (not shown) instead of, or in addition to the protrusion 106 to engage a corresponding protrusion (e.g., tongue) (not shown) that may be provided on the saddle 20 instead of, or in addition to the recess 206 to engage and hold the saddle 20 in the predetermined location in the coupling body 111.

Referring to FIG. 5B, the coupling assemblies 10 and 11 may include float area(s) C' to allow each coupling body 111 to rotate with respect to the saddle 20, clamp 40 and/or plate 30. The float area(s) C' may be formed by configuring the interface areas (or contact areas) between the interior walls of the receptacle 104 and the saddle 20, clamp 40 and/or plate 30, to provide sufficient clearance, or sufficiently low level of static friction, to allow the coupling body 111 to rotate with respect to the saddle 20, clamp 40 and/or plate 30. The float areas C' may be configured so as to allow for rotation of the coupling body 111 with respect to only clamp 40 and plate 30, while keeping the saddle 20 in fixed position with respect to the coupling body 111.

Referring back to FIG. 2, the bone fastener 50 may include a bone screw, such as, for example, any of the various pedicle screws common in the art. The bone fastener 50 may include the head portion 501, a neck portion 502, and a shaft portion 503. The bone fastener 50 may be configured at its distal end to penetrate and facilitate insertion of the bone fastener 50 into bone. At its proximal end, the head portion 501 may have a substantially spherical shape. The shaft portion 503 may have a thread 508 that is adapted to be screwed into a bone, such as, for example, a vertebra. Alternative formations may be formed in/on the shaft portion 503 which provide the intended purposes of securing the bone fastener 50 within a bone, as described herein. The shaft 503 may have a tapered shape, which may be provided with a high pitch thread. It is noted that the length, diameter, thread pitch, and thread diameter ratio of the shaft 503 may be selected based on the particular application of the bone fastener 50, as understood by those skilled in the art.

Figure 4:
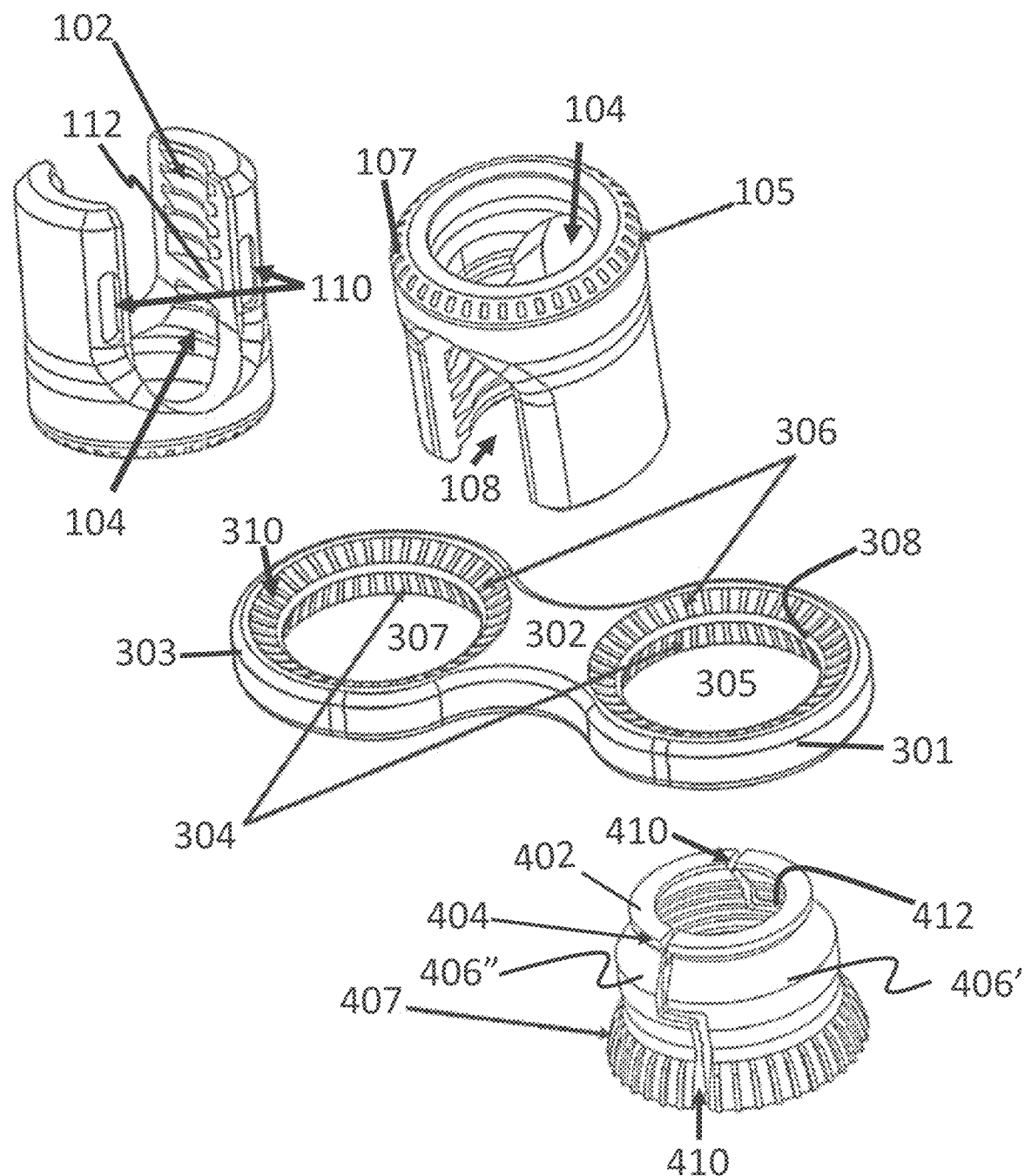
FIG. 4 shows examples of various components in the portion of the exemplary embodiment of the plate assembly shown in FIGS. 3A and 3B.

The head portion 501 may include a thread 506 on the circumference that is configured to engage the thread 412 in the clamp 40 (shown in FIG. 4). The head portion 501 may include a tool receptacle 504 at its proximal end that is configured to receive a driver tool (not shown) to, e.g., drive the fastener 50 into bone. The tool receptacle 504 may have a hexagon shape, a torque-screw shape, or any other shape that may facilitate the bone fastener 50 being driven into a bone by the driver tool.

FIG. 4 shows examples of the coupling body 111, the plate 30, and the clamp 40 that may be included in the plate assembly 100.

Referring to FIGS. 2 and 4, the clamp 40 includes a proximal end portion 402, a distal end portion 408, and a wall 406. The wall 406 may have an annular shape. The proximal end portion 402 includes the lip portion(s) 404. The lip portion(s) 404 may be pushed toward and snapped into the distal surface portion 204 of the saddle 20, snapping into place and engaging the lip portion 214 of the saddle 20, as seen in FIG. 5B. Alternatively, the saddle 20 may be pushed toward and the lip portion 214 snapped onto the lip portion(s) 404 of the clamp 40. The wall 406 has an outer surface and an inner surface.

As seen in FIG. 4, the wall 406 may include, for example, a pair of wall portions 406', 406" that may be assembled together to form the wall. The edges of the wall portions 406', 406", which form space(s) 410 between the wall portions, may be offset (such as, for example, include a step configuration) as seen in FIG. 4, so that the wall portion 406' may be inserted first in the receptacle 104 and in the distal surface portion 204 of the saddle 20, before inserting the wall portion 406" into the same receptacle 104 and in the distal surface portion 204 of the same saddle 20. The edges of the wall portions 406', 406" may include, for example, a step configuration such that when the wall portion 406" is inserted into the receptacle 104 after the wall portion 406' is inserted, the wall portion 406" will be guided and properly aligned in the receptacle 104 (and the distal surface portion 204 of the saddle 20) by the edges of the wall portion 406' and the inner wall surface of the receptacle 104. The wall portions 406', 406" may be formed such that when both wall portions are installed in the receptacle 104, the outer surfaces of the wall portions 406', 406" contact and engage the inner wall surfaces of the receptacle 104, preventing the wall portions 406', 406" from being removed from the receptacle 104 without application of an extracting force. The contact areas between the outer surfaces of the wall portions 406', 406", and the inner wall surfaces of the receptacles 104 may provide sufficient clearance, or sufficiently low static friction so as to allow the inner wall surfaces of the receptacle 104 to move with respect to the outer surfaces of the wall portions 406', 406".

Alternatively, the wall 406 may be formed of a single wall portion that includes a single space 410 to permit the wall 406 to be compressed from a free-standing diameter to a smaller diameter, which may be depend on, for example, the magnitude of applied force, the resilience of the wall portion, and the width of the space 410. The space 410 may be formed as an offset gap (or step configuration), as seen in FIGS. 2 and 4, thereby providing enhanced structural integrity and strength to the clamp 40. The free-standing diameter may be the diameter of the wall 406 when no force is applied to the clamp 40. The wall 406 may be expanded from, for example, the free-standing diameter to a larger diameter. The wall 406 may be made of a resilient material, so that the wall 406 may be compressed or expanded by, for example, using a tool (not shown) or by hand. For instance, when installing the clamp 40 in the receptacle 104 of the coupling body 111, the distal end portion 408 may be compressed using the tool, and the proximal end 402 of the clamp 40 may be moved toward and into the receptacle 104, moving the clamp inward until the proximal end portion 402 of the clamp 40 is seated within the receptacle 104, and within the distal surface portion 204 of the saddle 20. The distal end portion 408 may be released to allow the wall 406 to expand in the receptacle 104 to, for example, the free-standing diameter of the wall 406.

The diameter of the inner wall surface of the receptacle 104 that contacts the outer surface of the wall 406 may be configured to be substantially equal to the free-standing diameter of the wall 406. Alternatively, the diameter of the inner wall surface of the receptacle 104 may be greater (or less) than the free-standing diameter of the wall 406. As noted earlier, the inner walls of the receptacle 104 and the wall 406 may be configured to provide sufficient clearance to allow the coupling body 111 to rotate with respect to the clamp 40.

In the example of the clamp 40 having a single wall portion, the space 410 may run along the entire height of the wall 406, such that the proximal end portion 402 of the clamp 40, including the lip portion 404, may be compressed radially inward. The space 410 may be offset, as noted above. This may facilitate insertion of the proximal end portion 402 into the portion 204 of the saddle 20. The wall 406 may be released to radially expand the diameter of the proximal end portion 402 to engage the lip portion 214 on the saddle 20. Alternatively (or additionally) the saddle 20 may be configured to expand, receive and engage the lip portion 404 of the clamp 40, with or without compression (or expansion) of the clamp 40. The wall 406 may be made of a resilient material, such as, for example, a resilient titanium, a resilient titanium composite, or the like, that retains an expanded configuration, absent an external force of sufficient force to compress (or bend) the material.

The inner surface of the wall 406 may include an internal thread 412. The thread 412 may be formed on an inner circumference of, for example, the wall portions 406', 406" (shown in FIG. 4). The internal thread 412 may include a helical thread. The thread 412 may be configured to engage a corresponding thread 506 on the head portion 501 of the bone fastener 50, as illustrated, for example, in FIG. 6B. The wall 406 may be configured to expand when receiving, for example, the head portion 501, and to snap back to, for example, the free-standing diameter when the head portion 501 is properly positioned in the clamp 40. The free-standing diameter of the inner surface of the wall 406 may be less than or substantially equal to the diameter of the head portion 501.

Alternatively (or additionally), the thread 412 may be used to receive and engage a corresponding thread on a clamp fastener (not shown) that may be inserted into the clamp 40. The clamp fastener (not shown) may further assist in securing the clamp 40 in the receptacle 104. The clamp fastener may include a shape that is contoured to match the shape of the inner surface(s) of the wall 406. For instance, the clamp fastener may include a shape similar to that of the head portion 501. The clamp fastener may include shapes, such as, for example, a spherical shape, a semi-spherical shape, an annular shape, or any other shape that may engage and secure the clamp 40 within the receptacle 104. The clamp fastener (not shown) may include a tool receptacle (not shown) that may receive and be engaged by a driver tool (not shown) to receive a force to drive the clamp fastener into the clamp 40, such as, for example, a rotational force that may screw the clamp fastener into the clamp 40.

As seen in FIGS. 2 and 3B, the clamp 40 includes a clamp-plate lock 407 that may be provided along a portion of or along the entire perimeter (and/or surface) of the distal end portion 408 of the clamp. The clamp-plate lock 407 is configured to contact and engage a corresponding plate-clamp lock 304 provided on the plate 30, as seen in FIG. 3B. The clamp-plate lock 407 may be beveled or angled, as seen in FIG. 3B, to assist in properly seating the distal end portion of the coupling body 111 atop and/or in the plate 30. The plate-clamp lock 304 may be beveled so as to match and engage the radially beveled surfaces of the clamp-plate lock 407, while further assisting in properly seating the distal end portion of the coupling body 111 atop and/or in the plate 30. The clamp-plate lock 407 may include male (or female) locking features that are configured to contact, guide and engage the plate-clamp lock 304, which may include corresponding female (or male) locking features, thereby securing and locking the clamp 40 with respect to the plate 30. According to a non-limiting embodiment of the disclosure, the male locking features may include a series of teeth and the female locking features may include a corresponding series of receivers that are configured receive and engage the series of teeth.

As noted above, the teeth may have any shape that is suitable to engage corresponding receivers for the teeth, including, for example, a semispherical shape, a rectangular shape, a pyramid shape, a cylinder shape, a diamond shape, an elliptical shape, or the like. As also noted above, the corresponding receivers for the teeth may include corresponding recesses that are configured to receive and securely hold the teeth, including, for example, a semispherical shaped recess, a rectangular shaped recess, a pyramid shaped recess, a cylindrical shaped recess, a diamond shaped recess, an elliptical shaped recess, or the like.

Referring to FIGS. 3B and 4, the plate 30 includes a plate body 302, the plate-clamp lock 304, and the plate-coupling lock 306. The plate body 302 includes a plate body portion 301. The plate body 302 may include a second plate body portion 303. The plate-clamp lock 304 and/or the plate-coupling lock 306 may be formed integrally with the plate body portion 301 (and/or 303), or the plate-clamp lock 304 and/or the plate-coupling lock 306 may be provided separately and securely affixed to the plate body portion 301 (and/or 303).

The plate body portion 301 includes an aperture 305 that is configured to receive and pass therethrough a portion of the clamp 40, including the proximal end portion 402, as seen in FIGS. 4 and 5A. The plate body portion 303 may include an aperture 307 that may be configured to receive and pass therethrough a portion of a second clamp 40, including the proximal end portion 402, as also seen in FIGS. 4 and 5A. The plate body portion 301 (and/or 303) may include an interface 308 between the plate-clamp lock 304 and plate-coupling lock 306, as seen in FIG. 3B. The interface 308 may be substantially flush with the inner-most perimeter of the plate-clamp lock 304 and plate-coupling lock 306, as seen in FIG. 4. Alternatively, the interface 308 may be configured to be inwardly projecting and include an interface lip 309, as seen in FIG. 3B. The interface 308 may be configured to help guide and position the clamp 40 in the receptacle 104 of the coupling body 111. The interface 308 may be configured to contact and engage a portion of the wall 406 of the clamp 40 to provide proper positioning of the clamp 40 in the receptacle 104 and/or plate 30.

The plate body portion 301 (and/or 303) is configured to contact and engage the distal end of the coupling body 111 on a first planar side, and further configured to contact and engage the distal end portion 408 of the clamp 40 on a second, opposite planar side, thereby securely and fixedly holding the coupling body 111 with respect to the clamp 40. As seen in FIGS. 3B and 4, the plate-coupling lock 306 may be provided on the first planar side of the plate body portion 301 and configured to contact and engage the coupling-plate lock 105 provided on the distal end portion of the coupling body 111. As seen, the plate-clamp lock 304 may be provided on the second, opposite planar side of the plate body portion 301 (or 303) and configured to contact and engage the clamp-plate lock 407 on the distal end portion 408 of the clamp 40.

Referring back to FIGS. 2 and 3B, according to a non-limiting example of a process for assembling the plate assembly 100, the saddle 20 may be inserted and installed in the receptacle 104 of the coupling body 111, with the proximal surface portion 202 being inserted into the receptacle 104 and facing the stop(s) 112. The proximal end portion(s) 402 of the clamp 40 may be aligned with and passed through the aperture 305 (or 307) in the plate 30. The opening of the receptacle 104 at the distal end portion of the coupling body 111 may be aligned with the proximal end portion(s) 402 of the clamp 40, and the distal end of the coupling body 111 (with saddle 20) and the proximal end portion(s) 402 of the clamp 40 (with plate 30) may be moved toward each other, thereby driving the proximal end portion(s) 402 of the clamp 40 into the receptacle 104 and the saddle 20, until the proximal end portion(s) 402 is properly seated in the distal surface portion 204 of the saddle 20 and engaging the lip portion 214. It is noted that the processes may be carried out substantially simultaneously for both coupling assemblies 10 and 11 and plate 30.

Alternatively, the distal surface portion 204 of the saddle 204 may be aligned with and attached to the proximal end portion(s) 402 of the clamp 40, wherein the lip portion 214 of the saddle 20 contacts and engages the lip portion(s) 404 of the clamp 40. In this regard, the proximal end of the clamp 40 may have been previously passed through the aperture 305 (or 307), or the saddle 20 together with the proximal end of the clamp 40 may have been passed through the aperture 305 (or 307) of the plate 30, before installing the saddle 20 and proximal end portion(s) 402 of the clamp 40 in the receptacle 104 of the coupling body 111.

Referring to FIGS. 3B and 4, in the example where the wall 406 includes wall portions 406', 406", the above described process may include aligning and passing the proximal end portion 402 of the wall portion 406' through the aperture 305 (or 307) in the plate 30. At substantially the same time (or at a different time), the opening of the receptacle 104 in the coupling body 111 may be aligned with the proximal end portion 402 of the wall portion 406', and the receptacle 104 (including saddle 20) and/or the proximal end portion 402 of the wall portion 406' (with plate 30) may be moved toward each other, thereby driving the proximal end portion 402 of the wall portion 406' into the receptacle 104 and the saddle 20, until the proximal end portion 402 is properly seated in the distal surface portion 204 of the saddle 20 and engaging the lip portion 214. Once the wall portion 406' is installed as described above, the process may be repeated with the wall portion 406", including aligning and passing the proximal end portion 402 of the wall portion 406" through the aperture 305 (or 307) in the plate 30, and driving the proximal end portion 402 into the same receptacle 104 and the same saddle 20, until the proximal end portion 402 of the wall portion 406" is properly seated in the distal surface portion 204 of the saddle 20 and engaging the lip portion 214.

As noted earlier, the clamp 40 may include a single wall portion with the space 410. In this example, the clamp 40 may be compressed and held in a compressed configuration when the proximal end portion 402 of the clamp 40 is inserted through the aperture 305 (or 307) and into the receptacle 104 and the distal surface portion 204 of the saddle 20. Alternatively, the clamp 40 may be inserted into the saddle 20, and the combination of the clamp 40 with saddle 20 may be inserted through the aperture 305 (or 307) into the receptacle 104. Once the saddle 20 and clamp 40 are installed in the receptacle 104, and the plate 30 sandwiched between the lower portion of the coupling body 111 and the upper surface of the plate 30, the process may be repeated for the second coupling assembly. As noted earlier, the process may be carried out substantially simultaneously for both coupling assemblies 10, 11.

When assembled, the coupling assemblies 10 and 11 in the plate assembly 100 may include float areas C', as discussed above with reference to FIG. 5B, so that the coupling assemblies (or components thereof such as the coupling bodies 111) may be rotated with respect to the plate 30. The plate assembly 100 may be coupled to a bone fastener 50 to provide the anchoring system 1, as discussed below. As also discussed below, the plate assembly 100 may be adjusted to a desired position, and a pair of stabilization elements 70 may be installed, adjusted (as desirable or necessary), and secured in the anchoring system 1 using the locking caps 60.

Figure 7A:
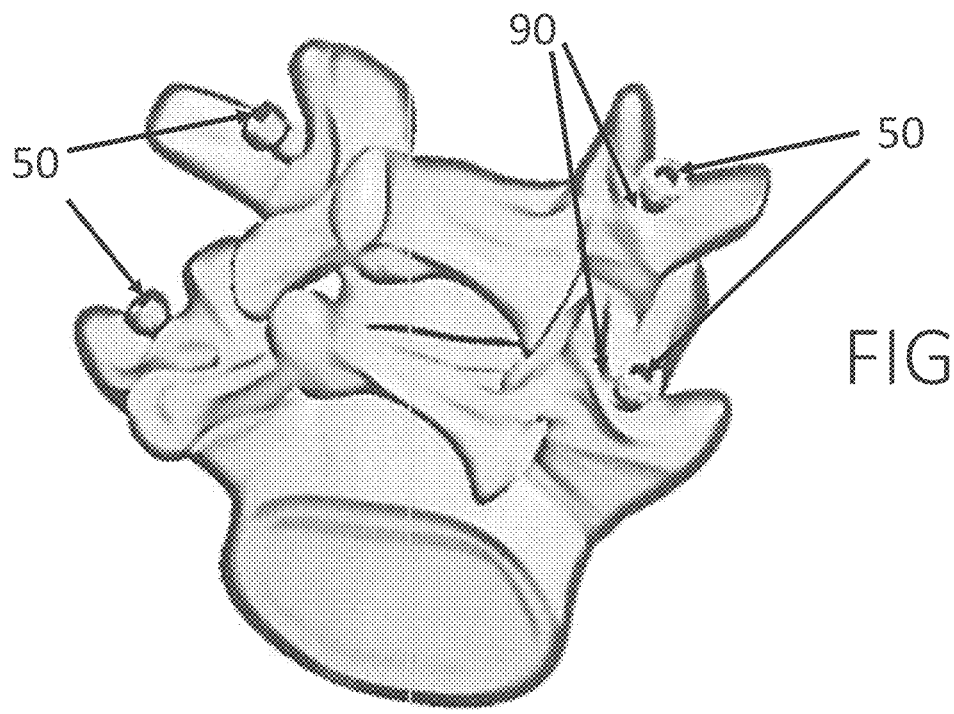
FIGS. 7A and 7B show various stages of implanting the exemplary anchoring system of FIGS. 1A and 1B into a bone.
Figure 7B:
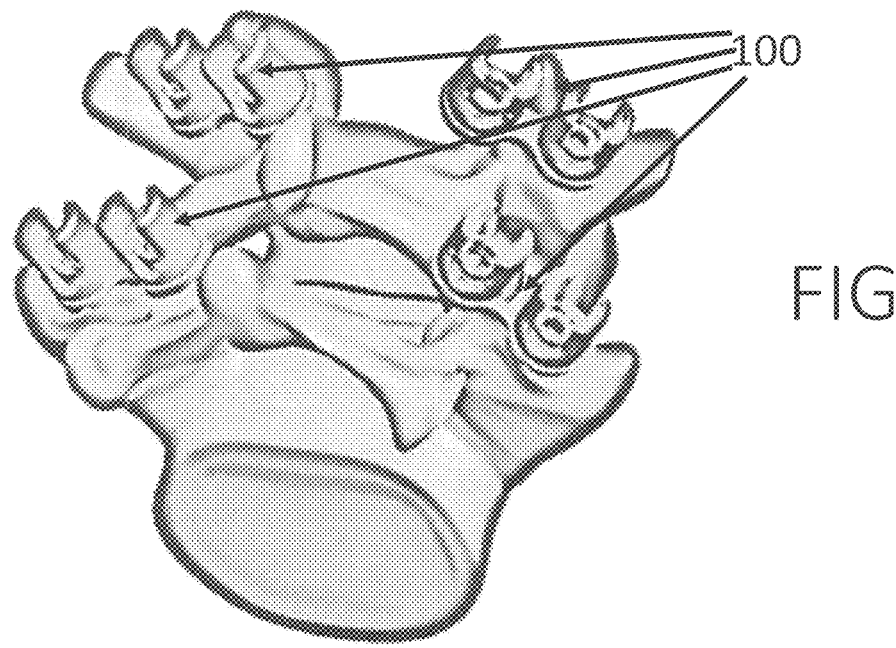

FIGS. 7A and 7B show various stages of implanting the exemplary anchoring system 1 into a bone, according to the principles of the disclosure, which will be referred to herein to describe a non-limiting example of an application of the disclosure.

Referring to FIG. 7A, after a surgical area is cleaned on a patient, an incision made, muscle tissue moved to the side(s), and other common surgical procedures carried out, tracks for the bone fasteners 50 may be prepared. In this regard, hard bone surface may be removed and a guide track may be inserted under x-ray guidance into, for example, the pedicle of the vertebrae. The depth and position of the guide track may be checked. Then, where the bone fastener 50 includes a bone screw, a thread may be tapped into the bone to form a tap 90 for the anchoring system 1. The process would be repeated for each implant of the anchoring system 1.

Using a driver tool (not shown), as is known by those skilled in the art, the driver tool may be moved toward and aligned with the bone fastener 50. The tool may contact the head portion 501 (shown in FIG. 2) of the bone fastener 50 and the driver tool may be manipulated until the driver tool head (not shown) is sufficiently seated in and engaged with the tool receptacle 504 in the bone fastener 50 (shown in FIG. 2) to ensure a secure connection. The driver tool, including the bone fastener 50, can then be aligned with the tap 90 in the bone and screwed into the threaded tap 90 in the bone using the driver tool. Alternatively, the bone fastener 50 may be partially installed in the tap 90 before being contacted by the driver tool. Once the bone fastener 50 is implanted in the desired position, the driver tool may be removed and the process repeated for each implant of the anchoring system 1.

Referring to FIG. 7B, after the bone fasteners 50 are securely and properly placed in the taps 90, a plate assembly 100 may be positioned proximate to the bone fastener 50, and the distal end portion 408 of the clamp 40 of the coupling assembly 10 (or 11) may be aligned with the head portion 501 of the bone fastener 50. Once properly aligned, the plate assembly 100 may be pressed toward and onto the head portion 501, forcing ("snapping") the head portion 501 into the clamp 40 and receptacle 104 of the coupling assembly 10 (or 11). This process may be repeated for each implant of the anchoring system 1.

FIGS. 7C-7G show various views of attaching and adjusting a plurality of stabilization elements 70 (e.g., rods) to the anchoring system 1 after it has been implanted in a bone.

Figure 7C:
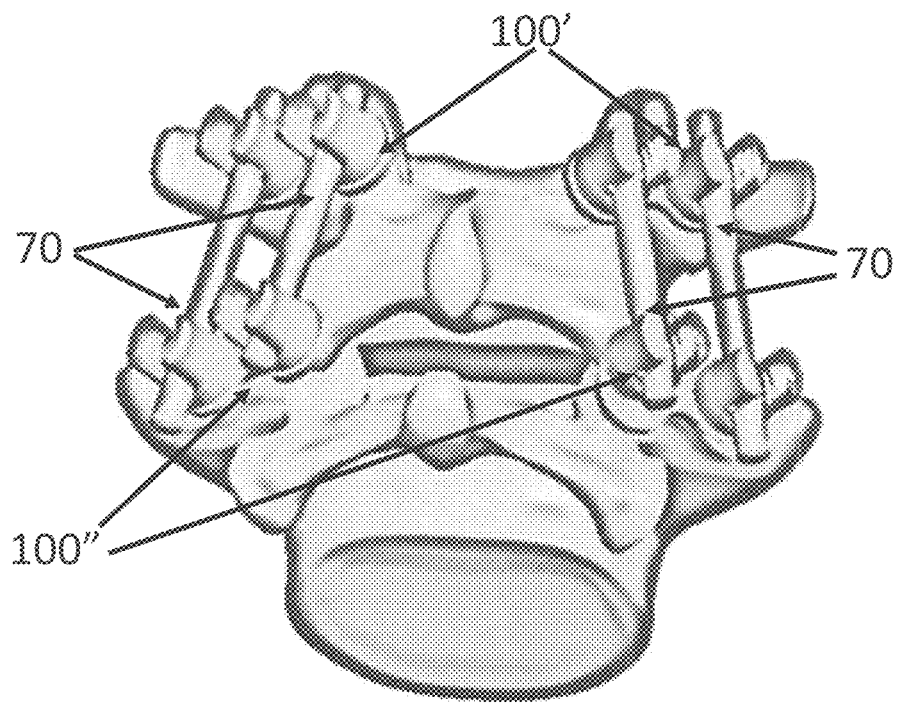
FIGS. 7C-7G show various views of attaching and adjusting a plurality of stabilization elements to the exemplary anchoring system after it has been implanted in a bone.

Referring to FIG. 7C, the plate assembly 100 (100' or 100") may be rotationally and/or angularly adjusted with respect to the bone fastener 50 to a desired position to allow for proper alignment and placement of the stabilization elements 70. The process may be repeated for each implant of the anchoring system 1. The stabilization elements 70 may be placed in each anchoring system 1. As seen, a pair of plate assemblies 100' located on a vertebra may be aligned with a corresponding pair of plate assemblies 100" located on an adjacent vertebra, so that the slots 108 in the coupling bodies 111 (shown in FIG. 3B) in the plate assemblies 100' may be aligned with the slots 108 in the coupling bodies 111 in the corresponding plate assemblies 100". The plate assemblies 100' and 100" of the pair of vertebrae may then be cross-connected using the stabilization elements 70 (e.g., elongate rods).

As seen in FIG. 7C, the adjacent plate assemblies 100', 100" may be coupled to a pair of stabilization elements 70 that are substantially the same (e.g., a pair of elongated rods). Alternatively, the pair of stabilization elements 70 may be different from each other. For instance, one of the stabilization elements may be an elongated rod that is coupled to both of the adjacent plate assemblies 100' and 100"; whereas, the other stabilization element may be a cross-brace that may have one end connected to plate assembly 100' or 100" and the other end coupled to another portion of the implant construct, such as, for example, a plate assembly, a stabilization element, a bone fastener, or the like.

Figure 7D:
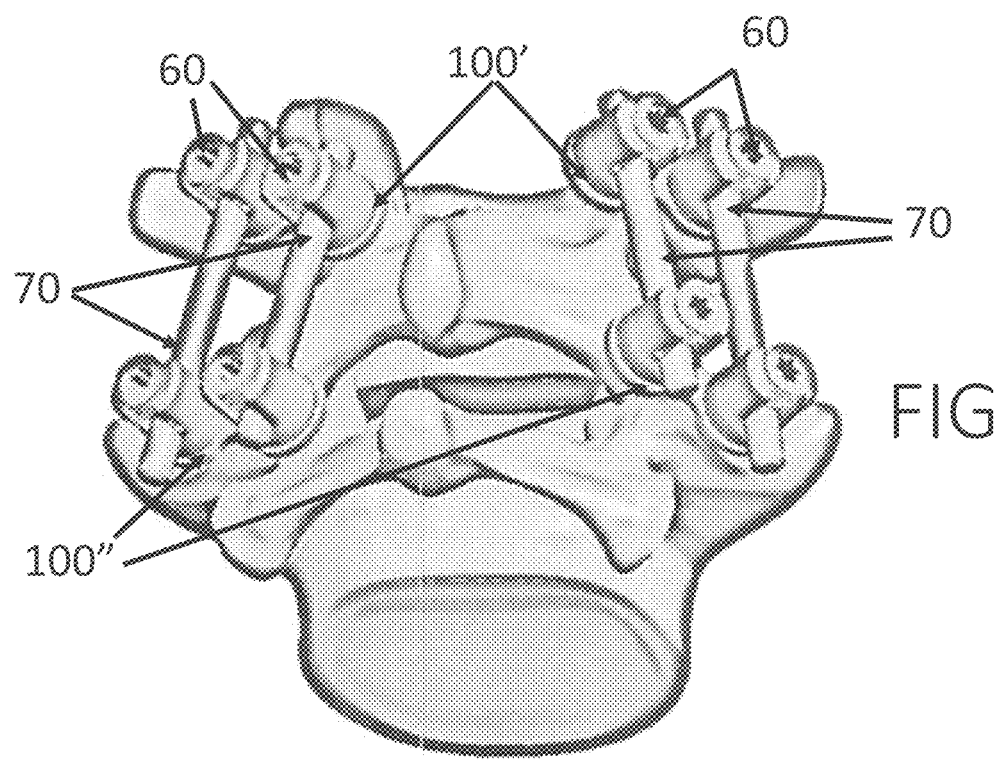

Referring to FIGS. 6A, 6B and 7D, with the stabilization elements 70 in place, using for example a cap driver (not shown) to engage a drive socket 62 on the locking cap 60, the cap driver may be operated to drive (e.g., screw) the locking cap 60 in a direction 84 into each coupling assembly 10, 11 of the plate assemblies 100' and 100", but stop driving the cap 60 so as to hold, but not lock the stabilization element 70 in place. For instance, the locking caps 60 may be positioned such that they keep the stabilization elements 70 captured in the plate assemblies 100', 100", but may allow for angular and/or rotational movement of the coupling assemblies 10, 11 with respect to the plate 30 and/or the bone fastener 50 to which the plate assembly is attached.

Figure 7E:
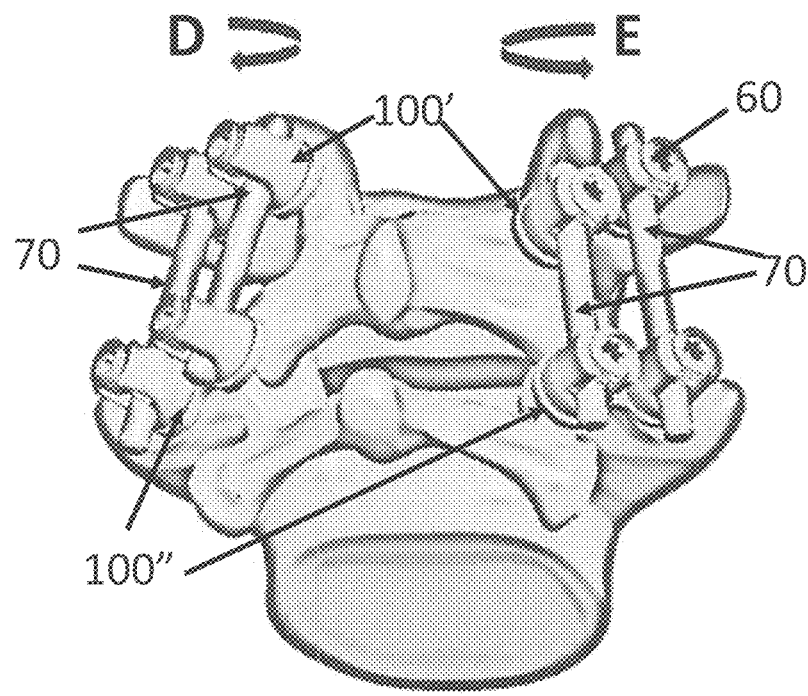

Referring to FIG. 7E, with the locking caps 60 and stabilization elements 70 in place, the plate assemblies 100', 100" (with stabilization elements 70) may be rotated, as shown by arrows D and E, to position the plate assemblies 100', 100" and stabilization elements 70 to a desired position. The plate assemblies 100', 100" (with stabilization elements 70) may be pivoted or angularly adjusted to a desired position. As the plate assemblies 100', 100" and stabilization elements 70 are rotated and/or pivoted, the coupling assemblies 10, 11 of each plate assembly 100', 100" may be allowed to rotate with respect to the plate 30 (and/or the bone fastener 50) in the respective plate assembly 100', 100", as seen in FIG. 7E when compared to FIG. 7D. As seen in FIG. 7E, rotation or angular adjustment of the plate assembly 100' (or 100") will cause the other cross-lined plate assembly 100" (or 100') to move correspondingly, including the stabilization elements 70.

Figure 7F:
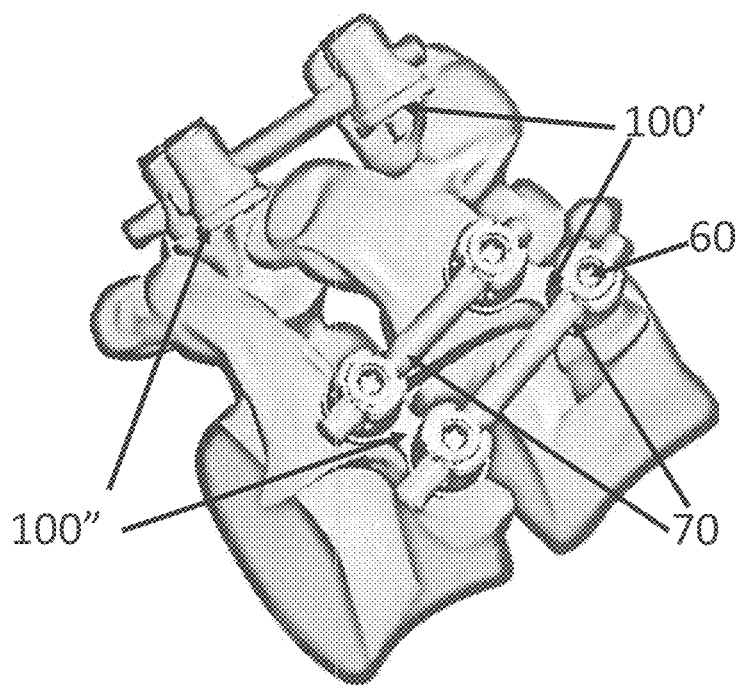

Referring to FIGS. 6B and 7F, once the plate assemblies 100', 100" and stabilization elements 70 are positioned as desired, using, for example, the cap driver (not shown), the locking cap 60 may be driven in the direction 84 toward the head portion 501 of the bone fastener 50. The distal surface of the locking cap 60 may be moved to contact a surface of the stabilization element 70 and, with movement of the locking cap in the direction 84, force the stabilization element 70 in the direction 84, thereby applying (or transferring) a force to the saddle 20 in the direction 84 toward the head portion 501, forcing the saddle 20 to compress and substantially simultaneously forcing the coupling body 111 in the direction 84 toward and into the plate 30, thereby locking the coupling body 111 to the plate 30. The movement of the coupling body 111 and/or saddle 20 in the direction 84 forces the clamp 40 to move in a substantially opposite direction 86, locking the head portion 501 of the bone fastener 50 in the clamp 40 (and receptacle 104) and moving the distal end portion of the clamp 40 toward (and into) the lower surface of the plate 30.

Figure 7G:
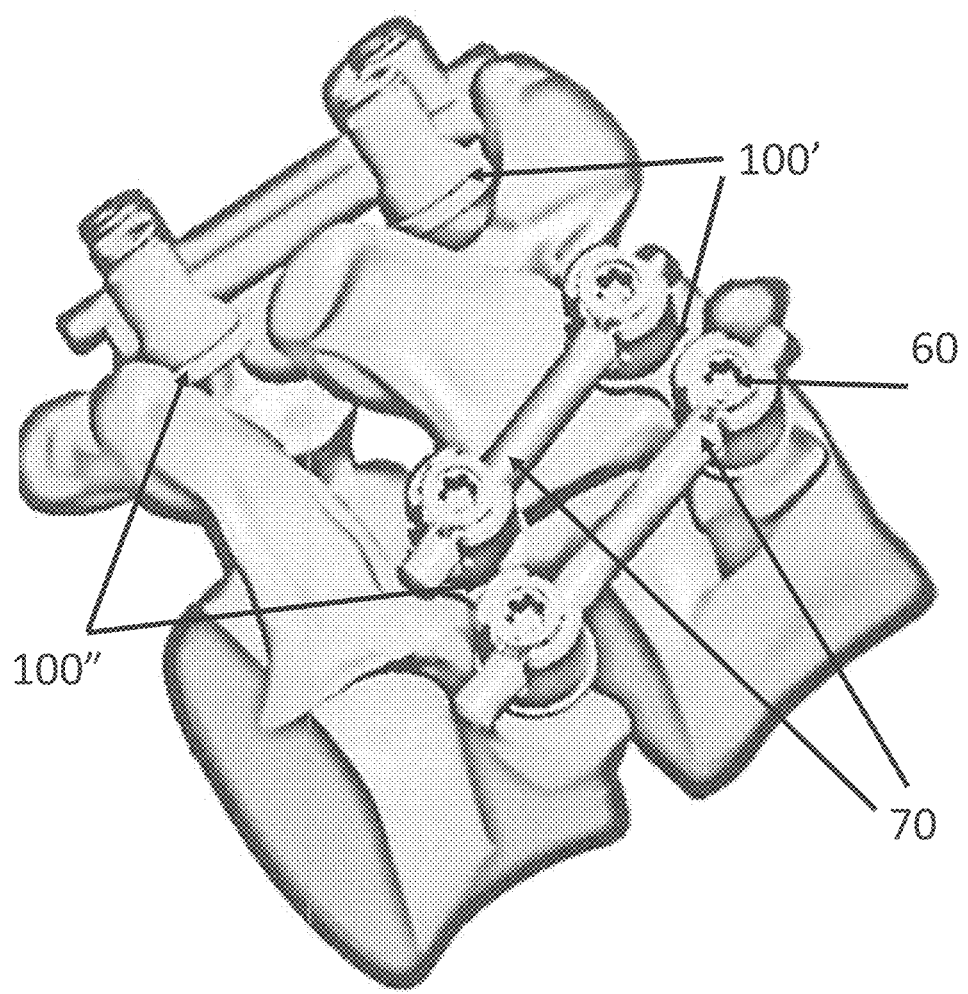

FIG. 7G shows a perspective side view of adjacent vertebrae with completed placement of the anchoring system 1 in the pedicles of the vertebrae. As seen, a pair of stabilization elements 70 (secured with locking caps 60) connect the adjacent anchoring systems on the vertebrae, thereby providing rigidity and stabilization between the anchoring systems.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed is:

1. A method for implanting an anchoring system in bone, the method comprising:
   providing an anchoring system, the anchoring system including:
      a first coupling assembly configured to receive and hold a first stabilization element;
      a second coupling assembly configured to receive and hold a second stabilization element; and
      a plate configured to attach to the first coupling assembly and to the second coupling assembly,
   implanting at least one bone screw in the bone;
   attaching the first coupling assembly to the at least one bone screw;
   coupling the first stabilization element to the first coupling assembly, wherein the first coupling assembly includes a first coupling body that receives and holds the first stabilization element;
   coupling the second coupling assembly of the anchoring system to the second stabilization element;
   coupling the plate to the first and second coupling assemblies, such that a portion of the plate is seated below the first coupling assembly and above a shaft of the bone screw; and
   inserting a first clamp into the first coupling assembly, wherein the first clamp includes a clamp-plate lock configured to engage a plate-clamp lock of the plate to lock the first clamp with respect to the plate,
   wherein the plate includes a plate-coupling lock configured to lock the plate to the first coupling body, wherein the first coupling body includes a coupling-plate lock that contacts and engages the plate-coupling lock to lock the plate to the first coupling body, and
   wherein the plate-coupling lock includes male locking features and the coupling-plate lock includes female locking features configured to receive the male locking features.

2. The method of claim 1, wherein the first coupling assembly includes:
   a first saddle configured to seat the first stabilization element.

3. The method of claim 2, wherein the second coupling assembly includes:
   a second coupling body that receives and holds the second stabilization element; and
   a second clamp that fastens the second coupling body to the plate.

4. The method of claim 3, wherein the first coupling body and the second coupling body are independently rotatable when the first coupling assembly is attached to a bone screw.

5. The method of claim 2, wherein at least one of the first coupling body and the first clamp includes a float area to allow the first coupling body to rotate with respect to the first clamp.

6. The method of claim 2, wherein the first saddle is configured to attach to the first clamp.

7. The method of claim 6, wherein the first coupling body includes a cap retainer that receives a locking cap that transfers and applies a force in a first direction to a portion of the first stabilization element and to a portion of the first saddle, wherein the first direction is towards the first clamp.

8. The method of claim 7, wherein the force causes the first clamp to travel in a second direction to lock the first clamp to the plate, wherein the second direction is substantially opposite to the first direction.

9. The method of claim 1, wherein the clamp-plate lock is beveled.

10. The method of claim 1, wherein the first coupling assembly, the second coupling assembly, and the plate are simultaneously rotationally and angularly adjustable with respect to the bone screw.

11. A method for implanting an anchoring system in bone, the method comprising:
    providing an anchoring system, the anchoring system including:
       a first coupling assembly configured to receive and hold a first stabilization element;
       a second coupling assembly configured to receive and hold a second stabilization element; and
       a plate that attaches to the first coupling assembly and to the second coupling assembly,
    implanting at least one bone screw in the bone;
    attaching the first coupling assembly of the anchoring system to the at least one bone screw;
    coupling the first stabilization element to the first coupling assembly, wherein the first coupling assembly includes a first coupling body that receives and holds the first stabilization element;
    coupling the second coupling assembly of the anchoring system to the second stabilization element;
    coupling the plate to the first and second coupling assemblies, such that a portion of the plate is seated below the first coupling assembly and above a shaft of the bone screw; and
    inserting a first clamp into the first coupling assembly, wherein the first clamp includes a clamp-plate lock configured to engage a plate-clamp lock of the plate to lock the first clamp with respect to the plate,
    wherein the first coupling body includes a cap retainer that receives a locking cap to secure the first coupling body and the first clamp to the plate,
    wherein the plate includes a plate-coupling lock configured to lock the plate to the first coupling body, wherein the first coupling body includes a coupling-plate lock that contacts and engages the plate-coupling lock to lock the plate to the first coupling body, and
    wherein the plate-coupling lock includes male locking features and the coupling-plate lock includes female locking features configured to receive the male locking features.

12. The method of claim 11, wherein the first coupling assembly includes:
    a first saddle configured to seat the first stabilization element.

13. The method of claim 12, wherein the second coupling assembly includes:
    a second coupling body that receives and holds the second stabilization element; and
    a second clamp that fastens the second coupling body to the plate.

14. The method of claim 13, wherein the first coupling body and the second coupling body are independently rotatable when the first coupling assembly is attached to a bone screw.

15. The method of claim 12, wherein at least one of the first coupling body and the first clamp includes a float area to allow the first coupling body to rotate with respect to the first clamp.

16. The method of claim 12, wherein the first saddle is configured to attach to the first clamp.

17. The method of claim 16, wherein the cap retainer transfers and applies a force in a first direction to a portion of the first stabilization element and to a portion of the first saddle, wherein the first direction is towards the first clamp.

18. The method of claim 17, wherein the force causes the first clamp to travel in a second direction to lock the first clamp to the plate, wherein the second direction is substantially opposite to the first direction.

19. The method of claim 11, wherein the clamp-plate lock is beveled.

20. The method of claim 11, wherein the first coupling assembly, the second coupling assembly, and the plate are simultaneously rotationally and angularly adjustable with respect to the bone screw.

\* \* \* \* \*